United States Patent
Borges et al.

(10) Patent No.: US 9,603,935 B2
(45) Date of Patent: Mar. 28, 2017

(54) ORAL DISPERSIBLE FILMS

(71) Applicant: Bluepharma, Coimbra (PT)

(72) Inventors: Ana Filipa Silva Borges, Coimbra (PT); Branca Margarida Almeida Silva, Coimbra (PT); Jorge Fernando Jordao Coelho, Coimbra (PT); Claudia Sousa Silva, Coimbra (PT); Sergio Paulo Simoes, Coimbra (PT)

(73) Assignee: Bluepharma, Coimbra (PT)

( * ) Notice: Subject to any disclaimer, the term of this patent is extended or adjusted under 35 U.S.C. 154(b) by 0 days.

(21) Appl. No.: 14/448,438

(22) Filed: Jul. 31, 2014

(65) Prior Publication Data

US 2015/0038594 A1     Feb. 5, 2015

Related U.S. Application Data

(60) Provisional application No. 61/860,516, filed on Jul. 31, 2013.

(51) Int. Cl.
| | | |
|---|---|---|
| *A01N 29/12* | (2006.01) | |
| *A61K 31/03* | (2006.01) | |
| *A61K 47/38* | (2006.01) | |
| *A61K 9/00* | (2006.01) | |
| *A61K 47/14* | (2017.01) | |
| *A61K 47/32* | (2006.01) | |

(52) U.S. Cl.
CPC .............. *A61K 47/38* (2013.01); *A61K 9/006* (2013.01); *A61K 9/0053* (2013.01); *A61K 9/0056* (2013.01); *A61K 47/14* (2013.01); *A61K 47/32* (2013.01)

(58) Field of Classification Search
None
See application file for complete search history.

(56) References Cited

U.S. PATENT DOCUMENTS

2006/0204587 A1*  9/2006  Kolter et al. ................ 424/490

FOREIGN PATENT DOCUMENTS

| EP | 0 381 194 A2 | 8/1990 |
| EP | 2 332 523 A1 | 6/2011 |

OTHER PUBLICATIONS

Jadhav et al, Int. J. Pharm Sci, vol. 4, Suppl 1, 337-341.*
Arya et al, Int.J. Chem. Tech. Res.2010,2(1).*
Invitation to Pay Additional Fees for PCT/PT2014/000050 mailed Nov. 10, 2014.
International Search Report and Written Opinion mailed Jan. 30, 2015 for Application No. PCT/PT2014/000050.
Pathare et al., Polymers used for fast disintegrating oral films: a review. Int J of Pharm Sci Rev Res. Jan. 1, 2013; 21(1):169-78.
International Preliminary Report on Patentability for PCT/PT2014/000050 mailed Feb. 11, 2016.

* cited by examiner

*Primary Examiner* — Jean Cornet
(74) *Attorney, Agent, or Firm* — Wolf, Greenfield & Sacks, P.C.

(57) ABSTRACT

Described herein are orodispersible films comprising a film forming hydrophobic polymer, a disintegrant, a plasticizer and a stabilizer.

27 Claims, No Drawings

ORAL DISPERSIBLE FILMS

RELATED APPLICATIONS

This Application claims priority under 35 U.S.C. §119(e) to U.S. Provisional Application Ser. No. 61/860,516, entitled "ORAL DISPERSIBLE FILMS" filed on Jul. 31, 2013, which is herein incorporated by reference in its entirety.

BACKGROUND OF THE INVENTION

Oral dispersible films have been introduced in the market as an alternative to conventional oral dosage forms to enhance patient compliance. For example, mucoadhesive film formulations have been described that improve absorption of pharmaceutical agents through the mucosal tissue to bypass barriers in the gastrointestinal tract. Oral dispersible films also can overcome the swallowing problems associated with the capsules or tablets. Many of the oral dispersible films that have previously been disclosed are designed for delivering a particular pharmaceutical agent. It is desirable to develop an oral dispersible film with a matrix flexible enough to incorporate a variety of agents, e.g. pharmaceutical agents, nutraceutical agents, dietary supplements, or cosmetic agents.

Oral dispersible films that are currently available can become sticky over time when exposed to ordinary environment conditions, even at minimal humidity, leading to low stability and undesirable texture and appearance. Typically oral dispersible films employ hydrophilic polymers as film forming agents, which can exacerbate stability issues due to their water-soluble nature. Even formulations proposed to overcome these issues have been based on hydrophilic polymers, as described in US 2004/0247648 and US 2011/0293673 (disclosing modified starch and a mixture of polyvinylpyrrolidone, and hydroxypropylcellulose, respectively).

Current oral dispersible films typically are able to carry and deliver only relatively low percentage by weight of an active agent. High loading of active agent in the film tends to interfere with film formation, film stability and desirable film properties.

There is a need for development of an oral dispersible film dosage form having flexibility for use with various agents, particularly at high active agent content, and having increased chemical stability and resistance to room and environmental conditions without compromising rapid disintegration time, texture and appearance.

DETAILED DESCRIPTION OF CERTAIN EMBODIMENTS OF THE INVENTION

The present disclosure relates to an edible film comprising (i) a film-forming polymer, (ii) a disintegrant, and (iii) a stabilizer that is one or both of polyvinyl alcohol (PVA) and hydroxypropylmethyl cellulose (HPMC). In certain embodiments, a provided film comprises only one of PVA or HPMC. In certain embodiments, the film forming polymer is not hydrophilic. In certain embodiments, the film forming polymer is hydrophobic. In certain embodiments, a provided film further includes a plasticizer. In embodiments, a provided film comprises one or more film forming polymer dispersants. In any of the embodiments, the film forming polymer comprises one or more active agents.

In certain embodiments, an orodispersible film described herein is prepared from an aqueous solution without any preservative or gelling additives. In certain embodiments, a provided oral dispersible film contains only one film-forming agent. In any of the foregoing embodiments, a provided oral dispersible film may contain one or more active agents (e.g., pharmaceutical agent, nutraceutical agent, cosmetic agent, supplement). In certain embodiments, a provided oral dispersible film displays rapid disintegration.

Although there are several oral dispersible films currently available, they suffer from various disadvantages. The present invention aims to ameliorate one or more of these disadvantages by providing one or more of reduced sticky sensation, enhanced moisture stability, easy handling, clean mouth feel, higher active agent loading and/or rapid disintegration. In certain embodiments, compositions provided herein have the advantage of improved stability and ease of manufacturing due to being less sensitive to the relative humidity than current oral films.

In certain embodiments, a provided oral dispersible film comprises a disintegrant and a hydrophobic film forming polymer. In certain embodiments, rapid disintegration time is not affected by the incorporation of a hydrophobic film forming polymer. In certain embodiments, a provided film is produced from an aqueous solution or suspension, rather than using organic solvents. In certain embodiments, a provided film is produced from a water/ethanol mixture.

In certain embodiments, a film-forming polymer provides a film-forming matrix for a provided film. In certain embodiments, the film forming polymer of a provided oral dispersible film has one or more of the following attributes: it is not toxic and/or it is not an irritant; it has good wetting and spreadability properties; it has suitable mechanical properties; it is tasteless; it is readily available; it is inexpensive; it provides rapid disintegration time; and/or it rapidly dissolves on the tongue or in the buccal cavity.

Film-forming polymers included in traditional oral dispersible films are generally characterized by charged or polar side groups on their structure that preferentially attract water, and thus they are generally categorized as hydrophilic, water-soluble and/or water swellable. Water-soluble film forming polymers include some cellulose derivatives containing hydrophilic groups, such as cellulose ethers (e.g., hydroxypropylmethyl cellulose, hydroxypropyl cellulose, hydroxyethyl cellulose, sodium carboxy methyl cellulose (Na—CMC)), starch and derivatives thereof (e.g., maltodextrins, pullulan, gelatin, gums (e.g., gum acacia, gum arabic, xanthan gum), pectin, chitosan derivatives, dextran, carrageenan, hyaluronic acid), poly(ethylene glycol) (PEG), polyvinyl pyrrolidone, polyvinyl pyrrolidone-vinyl acetate copolymer, polyvinyl alcohol, polyacrylic acid, divinyl ether-maleic anhydride, polyphosphazene, polyphosphates, polyphosphonates, poly(2-alkyl-2-oxazolines), N-(2-hydroxypropyl) methacrylamide, and polyacrylamide.

According to the present invention, films provided herein employ film forming polymers that are not hydrophilic, such as water-insoluble polymers, non-swellable polymers and/or hydrophobic polymers. Exemplary water-insoluble polymers include, but are not limited to, ethyl cellulose, hydroxypropyl ethyl cellulose, cellulose acetate phthalate, hydroxypropyl methyl cellulose phthalate, acrylic polymers (e.g., methacrylate copolymer, e.g., methyl methacrylate-diethylaminoethyl methacrylate copolymer), polyvinyl acetate, sodium sulphonated polyesters, carboxylated acrylics and shellac.

The film forming polymer is typically the main component of the films of the invention, other than the active agent. In certain embodiments, a provided film comprises a hydrophobic film-forming polymer in a range from about 40% to 99% by weight in the polymer component without the active substance, and 19% to 99% when including between 0.01% to 60% by weight of active substance. In certain embodiments, the film forming polymer represents about 19% to about 95% based on the dry weight of all the components of the film. In certain embodiments, the film-forming polymer represents about 19% to about 70% based on the dry weight of all the components of the film. In certain embodiments, the film-forming polymer represents about 19% to about 60% based on the dry weight of all the components of the film. In certain embodiments, the film-forming polymer represents about 30% to about 50% based on the dry weight of all the components of the film. In certain embodiments, the film-forming polymer represents about 19%, about 25%, about 30%, about 35%, about 40%, about 45%, about 50%, about 55%, about 60%, about 65%, about 70%, about 75%, about 80%, about 85%, about 90%, or about 95% based on the dry weight of all the components of the film.

It will be understood that when a range is recited in the application, the ends of the range are specifically disclosed as if specifically recited. For example, a range of 19%-99% specifically include a disclosure separately of 19% and separately of 99%.

In embodiments, oral dispersible films provided herein also include a disintegrant. A disintegrant facilitates the break-up of the film-forming matrix in an aqueous medium. Exemplary disintegrants include, but are not limited to, sugar alcohols, such as mannitol, sorbitol, xylitol, erythritol, lactitol, and maltitol; starches and starch derivatives such as pregelatinized starch and hydroxypropyl starch; cellulose derivatives, such as carboxymethylcellulose, croscarmellose, low-substituted hydroxypropyl cellulose and microcrystalline cellulose; and others disintegrants such as polacrilin potassium, glycine, crospovidone and magnesium aluminum silicate. In certain embodiments, the disintegrant is carboxymethylcellulose or a salt thereof. In certain embodiments, the disintegrant is sodium carboxymethylcellulose. In certain embodiments, the amount of disintegrant employed in a provided film depends on the nature of the polymer matrix and the rate of disintegration desired. In certain embodiments, the disintegrant represents about 0.5% to about 22% based on the dry weight of the formulation. In certain embodiments, the disintegrant represents about 2.5% to 17.5% based on the dry weight of all the components of the film. In certain embodiments, the disintegrant represents about 5% to 17.5% based on the dry weight of all the components of the film. In certain embodiments, the disintegrant represents about 5% to 15% based on the dry weight of all the components of the film.

In embodiments, a provided film comprises a stabilizer that is one or both of PVA and HPMC. In certain embodiments, a provided film includes either PVA or HPMC. In certain embodiments, a stabilizer represents about 0.1% to about 21% based on the dry weight of all the components of the film. In certain embodiments, a stabilizer represents about 0.5% to about 21% based on the dry weight of all the components of the film. In certain embodiments, a stabilizer represents about 1% to about 21% based on the dry weight of all the components of the film. In certain embodiments, a stabilizer represents about 2.5% to about 17.5% based on the dry weight of all the components of the film. In certain embodiments, a stabilizer represents about 5% to about 17.5% based on the dry weight of all the components of the film. In certain embodiments, a stabilizer represents about 5% to about 15% based on the dry weight of all the components of the film. In certain embodiments, a stabilizer employed in a provided film has low molecular weight less than 205 000 g/mol. In certain embodiments, a stabilizer employed in a provided film has low molecular weight, such as less than 100 000 g/mol. In certain embodiments, a stabilizer employed in a provided film has low molecular weight, such as less than 37 000 g/mol. In certain embodiments, a stabilizer employed in a provided film has low molecular weight, such as less than 11 000 g/mol.

In embodiments, the ratio of the film forming polymer to the stabilizer is about 20:1 to about 1:2 weight per weight. In certain embodiments, the ratio of the film forming polymer to the stabilizer is about 15:1 to about 1:1 weight per weight. In certain embodiments, the ratio of the film forming polymer to the stabilizer is about 11:1 to about 1:1 weight per weight. In certain embodiments, the ratio of the film forming polymer to the stabilizer is about 1:1, 2:1, 3:1, 4:1, 5:1, 6:1, 7:1, 8:1, 9:1, 10:1, or 11:1 weight per weight. In some embodiments, the film forming polymer is polyvinyl acetate, which represents about 30% to about 80% based on the dry weight of all the components of the film, and the stabilizer is polyvinyl alcohol present at a ratio of between 11:1 and 1:1 weight per weight of polyvinyl acetate:polyvinyl alcohol. In some embodiments, the film forming polymer is methacrylate copolymer, which represents about 19% to about 65% based on the dry weight of all the components of the film, and the stabilizer is polyvinyl alcohol present at a ratio of between 6:1 and 2:1 weight per weight of methacrylate copolymer:polyvinyl alcohol. In some embodiments, the film forming polymer is shellac, which represents about 30% to about 65% based on the dry weight of all the components of the film, and the stabilizer is hydroxypropylmethylcellulose present at a ratio of between 5:1 and 1:1 weight per weight of shellac:hydroxypropylmethylcellulose.

Other components can be added to provided films, including but not limited to, plasticizers, film forming polymer dispersants, surfactants, preservatives, taste masking agents, sweeteners, flavor and coloring agents, anti-foam agents, penetration enhancers, saliva stimulating agents, buffering agents, thickening agents, enzyme inhibitors, and solubilizers.

In certain embodiments, a provided film comprises a plasticizer. Exemplary plasticizers include, but are not limited to, phthalate derivatives (e.g., dimethyl phthalate, diethyl phthalate, dibutyl phthalate), citrate derivatives (e.g., tributylcitrate, triethylcitrate, acetyl citrate, citric acid), polyalkylene oxides (e.g., polyethylene glycols, polypropylene glycols, polyethylene-propylene glycols), glycerol, glycerol monoacetate, glycerol diacetate, triacetate, triacetin, polysorbate, cetyl alcohol, propylene glycol, sorbitol, sodium diethylsulfosuccinate, and castor oil. In certain embodiments, a plasticizer represents 0% to about 30% based on the dry weight of all the components of the film. In certain embodiments, a plasticizer represents about 1% to about 20% based on the dry weight of all the components of the film. In certain embodiments, a plasticizer represents about 2.5% to about 17.5% based on the dry weight of all the components of the film. In certain embodiments, a plasticizer represents about 2.5% to about 10% based on the dry weight of all the components of the film.

In certain embodiments, the provided film comprises a dispersant for the film forming polymer. Film forming polymers are often supplied as a solution containing dispersants for maintaining stability of the film forming polymer dispersion. For example, polyvinyl acetate can be supplied with dispersants such as sodium lauryl sulfate and povidone. As another example, methacrylate copolymer can be supplied with macrogol cetostearyl ether and sodium lauryl sulfate, or sorbic acid and sodium hydroxide as dispersants.

The dispersant(s) typically are present in amounts from 0.001% to 10% based on the dry weight of all the components of the film. In certain embodiments, the dispersant is present in amounts ranging from 0.01% to 8% based on the dry weight of all the components of the film. In certain embodiments, a dispersant is present in amounts ranging from 0.1% to 5% based on the dry weight of all the components of the film. In certain embodiments, a dispersant represents about 0.001% to about 1% based on the dry weight of all the components of the film. In certain embodiments, a dispersant represents about 0.04% to about 0.7% based on the dry weight of all the components of the film. In certain embodiments, a dispersant represents about 0.01% to about 7.5% based on the dry weight of all the components of the film.

In certain embodiments, a provided film comprises a sweetener. Sweeteners can be used to improve palatability and are usually classified as natural or artificial sweeteners. Exemplary natural sweeteners include, but are not limited to, dextrose, fructose, glucose, liquid glucose, maltose, rebiana, glycyrrhizin, thaumatin, sorbitol, mannitol, isomalt, maltitol, xylitol, and erythritol. Exemplary artificial sweeteners include, but are not limited to, saccharin, cyclamate, aspartame, acesulfame-K, sucralose, alitame and neotame. In certain embodiments, monoammonium glycyrrhizinate is used as a sweetener. In certain embodiments, neohespiridin dihydrochalcone is used as a sweetener. In certain embodiments, a sweetener represents about 0% to about 10% based on the dry weight of all the components of the film. In certain embodiments, a sweetener represents about 0.1% to about 10% based on the dry weight of all the components of the film. In certain embodiments, a sweetener represents about 1% to about 10% based on the dry weight of all the components of the film. In certain embodiments, a sweetener represents about 1% to about 7% based on the dry weight of all the components of the film. In certain embodiments, a sweetener represents about 1% to about 6% based on the dry weight of all the components of the film. In certain embodiments, a sweetener represents about 1% to about 5% based on the dry weight of all the components of the film.

In certain embodiments, a provided film comprises a saliva stimulant. Saliva stimulants can be added to increase the rate of saliva production in order to promote a faster disintegration of the orodispersible film. Exemplary saliva stimulants include, but are not limited to, acidic compounds as citric acid, malic acid, lactic acid, ascorbic acid and tartaric acid. In other embodiments, some sweeteners can be used as saliva stimulants, including but not limited to glucose, fructose, xylose, maltose, and lactose. In certain embodiments, a saliva stimulant represents about 0% to about 10% based on the dry weight of all the components of the film. In certain embodiments, a saliva stimulant represents about 0% to about 7% based on the dry weight of all the components of the film. In certain embodiments, a saliva stimulant represents 0% to about 6% based on the dry weight of all the components of the film. In certain embodiments, a saliva stimulant represents about 2% to about 6% based on the dry weight of all the components of the film.

In certain embodiments, a provided film comprises a buffering agent. Buffering agents can be added to manipulate the pH. The pH is involved in the dissolution and stabilization of the components in the formulation, but also with their absorption through the oral mucosa. Exemplary buffer agents include, but are not limited to citrate buffers, phosphate buffers, acetate buffers, carbonate buffers, ammonia buffers, borate buffers, lactate buffers, ethanolamine buffers, glycine buffers, methionine buffers, glutamate buffers and succinate buffers. In certain embodiments the pH buffer is an acid/acid salt system. Exemplary acid/acid salt systems include, but are not limited to, citric acid/citric acid salts (e.g. sodium citrate, potassium citrate), citric acid/phosphoric acid salts (e.g. sodium aluminium phosphate, sodium monobasic phosphate, sodium dibasic phosphate, sodium tribasic phosphate, potassium tribasic phosphate, potassium monobasic phosphate, potassium dibasic phosphate), citric acid/tartaric acid salts (e.g. sodium tartrate, potassium tartrate), citric acid/boric acid salts (e.g. sodium borate, potassium borate), citric acid/malic acid salts (e.g. sodium malate, potassium malate), citric acid/maleic acid salts (e.g. sodium maleate, potassium maleate), tartaric acid/citric acid salts (e.g. sodium citrate, potassium citrate), tartaric acid/phosphoric acid salts (e.g. sodium aluminium phosphate, sodium monobasic phosphate, sodium dibasic phosphate, sodium tribasic phosphate, potassium tribasic phosphate, potassium monobasic phosphate, potassium dibasic phosphate), tartaric acid/tartaric acid salts (e.g. sodium tartrate, potassium tartrate), tartaric acid/boric acid salts (e.g. sodium borate, potassium borate), tartaric acid/malic acid salts (e.g. sodium malate, potassium malate), tartaric acid/maleic acid salts (e.g. sodium maleate, potassium maleate), boric acid/citric acid salts (e.g. sodium citrate, potassium citrate), boric acid/phosphoric acid salts (e.g. sodium aluminium phosphate, sodium monobasic phosphate, sodium dibasic phosphate, sodium tribasic phosphate, potassium tribasic phosphate, potassium monobasic phosphate, potassium dibasic phosphate), boric acid/tartaric acid salts (e.g. sodium tartrate, potassium tartrate), boric acid/boric acid salts (e.g. sodium borate, potassium borate), boric acid/malic acid salts (e.g. sodium malate, potassium malate), boric acid/maleic acid salts (e.g. sodium maleate, potassium maleate), malic acid/citric acid salts (e.g. sodium citrate, potassium citrate), malic acid/phosphoric acid salts (e.g. sodium aluminium phosphate, sodium monobasic phosphate, sodium dibasic phosphate, sodium tribasic phosphate, potassium tribasic phosphate, potassium monobasic phosphate, potassium dibasic phosphate), malic acid/tartaric acid salts (e.g. sodium tartrate, potassium tartrate), malic acid/boric acid salts (e.g. sodium borate, potassium borate), malic acid/malic acid salts (e.g. sodium malate, potassium malate), malic acid/maleic acid salts (e.g. sodium maleate, potassium maleate), maleic acid/citric acid salts (e.g. sodium citrate, potassium citrate), maleic acid/phosphoric acid salts (e.g. sodium aluminium phosphate, sodium monobasic phosphate, sodium dibasic phosphate, sodium tribasic phosphate, potassium tribasic phosphate, potassium monobasic phosphate, potassium dibasic phosphate), maleic acid/tartaric acid salts (e.g. sodium tartrate, potassium tartrate), maleic acid/boric acid salts (e.g. sodium borate, potassium borate), maleic acid/malic acid salts (e.g. sodium malate, potassium malate), maleic acid/maleic acid salts (e.g. sodium maleate, potassium maleate). In certain embodiments, the buffer system represents about 0% to about 15% by weight of the film. In certain embodiments, a buffer system represents 0% to about 10% by weight of the film. In certain embodiments, a buffer system represents about 0% to about 7.5% by weight of the film.

In certain embodiments, a provided film comprises taste-masking agents. Taste-masking agents can be added to ameliorate the organoleptic characteristics of the orodispersible film. In certain embodiments, taste masking agents may be used to mask unpleasant taste of some components. Exemplary of taste-masking agents include, but are not limited to, cyclodextrins, maltodextrins, ion-exchange resins, amino acids, gelatin, gelatinized starch, liposomes, lecithins or lecithin-like substances and salts. In certain embodiments, the taste masking agent comprises about 0% to about 15% based on the dry weight of all the components of the film. In certain embodiments, the taste masking agent represents 0% to about 10% based on the dry weight of all the components of the film. In certain embodiments, the taste masking agent represents about 0% to about 7.5% based on the dry weight of all the components of the film. In certain embodiments, the taste masking agent represents about 0% to about 5% based on the dry weight of all the components of the film.

In certain embodiments, a provided film comprises a flavoring agent. In certain embodiments, flavoring agents may be natural flavors, derived from various parts of the plants like leaves, fruits and flowers, or synthetic flavor oils or powders. Exemplary flavor oils include, but are not limited to, peppermint oil, cinnamon oil, spearmint oil, and oil of nutmeg. Exemplary fruity flavors include, but are not limited to, vanilla, cocoa, coffee, chocolate and citrus. Exemplary fruit essence flavors include, but are not limited to, apple, raspberry, cherry, and pineapple. Flavors can be used alone or in the combination and its selection will be dependent upon the target population and any other substance (e.g., a pharmaceutical agent) incorporated in the film. The perception of the flavors changes from individual to individual and also with age: typically a geriatric population will prefer mint or orange flavors whereas younger populations tend to prefer flavors like fruit punch, raspberry, etc. Generally the amount of flavor needed to mask an unpleasant taste or improve taste overall will depend on the flavor type and its strength. In certain embodiments, a flavoring agent represents about 0% to about 10% based on the dry weight of all the components of the film. In certain embodiments, a flavoring agent represents about 1% to about 10% based on the dry weight of all the components of the film. In certain embodiments, a flavoring agent represents about 1% to about 6% based on the dry weight of all the components of the film.

Cooling agents may also be added in order to improve the aftertaste of an oral film formulation. Exemplary cooling agents include but are not limited to menthol flavor and some polyol sugars which are widely used for this purpose. In some embodiments, monoammonium glycyrrhizinate can be added to improve the flavor strength and extend sweetness. Other components can also be added that should compete with sensory stimuli, such as Cremophor (which is used to coat the surface protein receptors), or saline solutions (e.g. sodium chloride, which competes within channel receptors with the bitter stimuli to reduce the overall perception of bitterness). Additionally, cooling agent neohesperidin dihydrochalcone can also be used as a flavor and/or sweetener.

In certain embodiments, a provided film comprises a colorant. Colorants can be added to enhance the aesthetic appeal of the oral film, especially when formulation ingredients or drugs are presented in insoluble or suspension form. Generally, any colorant could be added, such as for example titanium dioxide or FD&C pigments. In certain embodiments, a colorant represents 0% to about 1% based on the dry weight of all the components of the film. In certain embodiments, a colorant represents about 0.001% to about 1% based on the dry weight of all the components of the film. In certain embodiments, a colorant represents about 0.1% to about 0.5% based on the dry weight of all the components of the film.

In certain embodiments, a provided film comprises a surfactant. Exemplary edible surfactants include, but are not limited to, sorbitan fatty acid esters (e.g., sorbitan monoisostearate, sorbitan monolaurate, sorbitan monooleate, sorbitan monopalmitate, sorbitan monostearate, sorbitan sesquistearate, sorbitan sesquioleate, sorbitan trilaurate, sorbitan trioleate, sorbitan tristearate), sucrose palmitate, glyceryl monooleate, vitamin E polyethylene glycol succinate, propylene glycol monolaurate, myristyl alcohol, polyoxyethylene alkyl ethers, polyoxyethylene castor oil derivatives, sodium lauryl sulfate, and propylene glycol dilaurate. In certain embodiments, a surfactant represents about 0.01% to about 5% based on the dry weight of all the components of the film. In certain embodiments, a surfactant represents about 0.4% to about 0.7% based on the dry weight of all the components of the film.

In certain embodiments, a provided film comprises: about 30-95% by weight of polyvinyl acetate as a film forming polymer; about 0.001-1% by weight of sodium lauryl sulfate as a film forming polymer dispersant; about 0.01-7.5% by weight of povidone as a film forming polymer dispersant; about 1-21% by weight of polyvinyl alcohol or hydroxypropylmethylcellulose as a stabilizer; and about 1-22% by weight of sodium carboxymethylcellulose as a disintegrant, wherein the total percentage by weight of all components does not exceed 100%. These proportions (and those that follow in this paragraph) are without taking into account the active substance to be included in the formulation. In certain embodiments, polyvinyl acetate comprises about 30-60% by weight of the film. In certain embodiments, the film comprises a polyvinyl acetate dispersion containing sodium lauryl sulfate and povidone as about 50% by weight of the film. In certain embodiments, povidone comprises about 1-6.5% by weight of the film. In certain embodiments, sodium lauryl sulfate comprises about 0.04-0.7% by weight of the film. In certain embodiments, polyvinyl alcohol or hydroxymethylcellulose comprises about 5-17.5% by weight of the film. In certain embodiments, polyvinyl alcohol comprises about 15% by weight of the film. In certain embodiments, the film includes a disintegrant. In certain embodiments, the disintegrant is sodium carboxymethylcellulose, present in an amount of about 5-20% by weight of the film. In certain embodiments, sodium carboxymethylcellulose comprises about 15% by weight of the film. In certain embodiments, the film further comprises triethylcitrate. In certain embodiments, the film further comprises triethylcitrate as about 5% by weight of the film.

In certain embodiments, the film further comprises citric acid. Citric acid can act as a plasticizer and also as a component of a buffer system. In certain embodiments, the film further comprises citric acid as about 3.5-7% based on the dry weight of all the components of the film. In certain embodiments, the film further comprises neohesperidine dihydrochalcone. In certain embodiments, the film further comprises neohesperidine dihydrochalcone as about 0.5-1% based on the dry weight of all the components of the film. In certain embodiments, the film further comprises sucralose. In certain embodiments, the film further comprises sucralose as about 0.5-5% based on the dry weight of all the components of the film. In certain embodiments, the film further comprises a flavoring agent. In certain embodiments, the film further comprises a flavoring agent as about 2.5-5% by weight of the film. In certain embodiments, the film further comprises a colorant. In certain embodiments, the film further comprises a colorant as about 0.5-1% by weight of the film.

In certain embodiments, a provided film comprises: about 30-95% by weight of shellac as a film forming polymer; about 1-21% by weight of polyvinyl alcohol or hydroxypropylmethylcellulose as a stabilizer; and about 1-22% by weight of sodium carboxymethylcellulose as a disintegrant, wherein the total percentage by weight of all components does not exceed 100%. These proportions (and those that follow in this paragraph) are without taking into account the active substance to be included in the formulation. In certain embodiments, shellac comprises about 30-60% by weight of the film. In certain embodiments, shellac comprises about 50% by weight of the film. In certain embodiments, polyvinyl alcohol or hydroxypropylmethylcellulose comprises about 5-17.5% by weight of the film. In certain embodiments, polyvinyl alcohol or hydroxypropylmethylcellulose comprises about 10-20% by weight of the film. In certain embodiments, hydroxypropylmethylcellulose comprises about 20% by weight of the film. In certain embodiments, sodium carboxymethylcellulose comprises about 5-20% by weight of the film. In certain embodiments, sodium carboxymethylcellulose comprises about 17.5% by weight of the film. In certain embodiments, the film further comprises propylene glycol. In certain embodiments, the film further comprises propylene glycol as about 9.5% by weight of the film. In certain embodiments, the film further comprises neohesperidine dihydrochalcone. In certain embodiments, the film further comprises sucralose. In certain embodiments, the film further comprises a flavoring agent. In certain embodiments, the film further comprises a colorant.

In certain embodiments, a provided film comprises: about 19-95% by weight of methacrylate copolymer as a film forming polymer; about 0.001-5% by weight of macrogol cetostearyl ether and sodium lauryl sulfate, or sorbic acid and sodium hydroxide, as film forming polymer dispersants; about 1-21% by weight of polyvinyl alcohol or hydroxypropylmethylcellulose as a stabilizer; and about 1-22% by weight of sodium carboxymethylcellulose as a disintegrant, wherein the total percentage by weight of all components does not exceed 100%. These proportions (and those that follow in this paragraph) are without taking into account the active substance to be included in the formulation. In certain embodiments, methacrylate copolymer comprises about 19-60% by weight of the film. In certain embodiments, the film comprises a methacrylate copolymer dispersion containing macrogol cetostearyl ether and sodium lauryl sulfate, or sorbic acid and sodium hydroxide as about 50%-60%, or about 55%, by weight of the film. In certain embodiments, polyvinyl alcohol or hydroxypropylmethylcellulose comprises about 5-17.5% by weight of the film. In certain embodiments, polyvinyl alcohol comprises about 15% by weight of the film. In certain embodiments, sodium carboxymethylcellulose comprises about 5-20% by weight of the film. In certain embodiments, sodium carboxymethylcellulose comprises about 20% by weight of the film. In certain embodiments, the film further comprises glycerol. In certain embodiments, the film further comprises glycerol as about 10% by weight of the film. In certain embodiments, the film further comprises neohesperidine dihydrochalcone. In certain embodiments, the film further comprises sucralose. In certain embodiments, the film further comprises a flavoring agent.

In any of the foregoing embodiments, a provided oral dispersible film may contain one or more active agents, e.g., pharmaceutical agent, nutraceutical agent, cosmetic agent, supplement. In embodiments, the active agent is included in an amount from about 0.001% to 60% based on the weight of all the components of the film. In embodiments, the active agent is included in an amount from about 0.1% to 45% based on the weight of all the components of the film. In embodiments, the active agent is included in an amount from about 1% to 40% based on the weight of all the components of the film.

In certain embodiments, a pharmaceutical agent is included in an oral dispersible film described herein. In certain embodiments, the oral dispersible film can be designed such that a pharmaceutical agent included therein has a local effect. In certain embodiments, the oral dispersible film can be designed such that a pharmaceutical agent included therein is absorbed by the oral mucosa. In certain embodiments, the oral dispersible film can be designed such that a pharmaceutical agent included therein mimics the pharmacokinetics of a traditional dosage form (e.g., an oral dosage form), such as a marketed dosage form, such as a capsule or tablet. Non-limiting examples of pharmaceutical agents that may be included in an oral dispersible film described herein include 5HT3 antagonists, Ace inhibitors, alcohols, alkaloid narcotics, alkaloids, alpha-1-adrenergic receptor antagonists, amides, amino acid preparations, anabolic preparations, barbiturate acid derivatives, benzodiazepines and derivatives, bromides, beta-adrenergic antagonists, dopamine D1/D2 antagonists, H2 antagonists, mineralocorticoids, monoamine oxidase inhibitors, acne drugs, agents for virulent carcinoma, Alzheimer's disease medicines, analeptics, analgesics, anesthetics, antacids, CGRP receptor antagonists, antiallergic medications, antianginal drugs, anti-anxiety agents, anti-arrrhythmias, antiasthmatics, antibiotics, anti-cholesterolemics, anticoagulants, anticonvulsants, antidepressants, antidiabetic drugs, anti-diarrhea preparations, anti-emetics, anti-epileptics, antifungals, antihistamines, anti-hypertensive drugs, anti-inflammatory drugs, anti-inflammatory anodynes, anti-inflammatory enzymes, anti-inflammatory steroids, anti-lipid agents, anti-malarials, anti-maniacs, anti-migraines, antinauseants, anti-neoplastics, anti-obesity drugs, antiparasitic agents, anti-Parkinsonian agents, anti-periodontitis agents, antipodagrics, antipsychotics, anti-pyretics, including analgesic anti-pyretics, anti-rheumatic agents, antispasmodic agents, anti-stroke agents, anti-thrombotic agents, anti-thyroid preparations, anti-tumor drugs, antitussives, anti-ulcer agents, anti-uricemic drugs, antivirals, appetite stimulants, appetite suppressants, awakening agents, biological response modifiers, blood coagulation inhibitors, blood modifiers, blood pressure depressing agents, blood vein dilating agents, blood vessel protective agents, bone metabolism regulators, bronchodilators, carbamates, cardiac strengthening agents, cardiotonic drugs, cardiovascular agents, central nervous system stimulants, cerebral circulation agents, cerebral dilators, chemically therapeutic agents, chemotherapeutics, narcotics, chloral derivatives, cholagogues, cholinesterase inhibitors, contraceptives, coronary dilators, cough curing agents, cough suppressants, decongestants, dermatological agents, diabetic angina agents, digesting organ curing agents, diuretics, DNA and genetic modifying drugs, drugs for renal failure, drugs for treating gastric disorders, drugs which selectively modify CNS function, hormone replacement therapies, emetic agents, endometriosis management agents, enzymes, erectile dysfunction therapies, erythiopoietic drugs, expectorants, fertility agents, gastrointestinal agents, glucocorticoids, steroids, hardening agents, hemostatic agents, homeopathic remedies, hormonal drugs, hormones, hyperglycemic agents, hypoglycemic agents, hypercalcemia and hypocalcemia management agents, hypnotics, hypolipidemic drugs, hypotensives, immunomodulators, immunosuppressives, intestinal regulators, ion exchange resins, laxatives, local anesthetic agents, local narcotic agents, lupus erythematosus agents, metabolism ameliorators, migraine treatments, miotic agents, motion sickness treatments, mucolytic agents, muscle relaxants, narcotic analgesics, narcotic antagonists, neuromuscular blocking agents, neuromuscular drugs, neuroprotective agents, non-cyclic ureides, nootropics, obesity management agents, ophthalmic agents, osteoporosis drugs, ovarian hormones, oxytocic agents, oxytocics, parasympatholytics, parasympathomimetics, pepsin inhibitors, peripheral vasodilators, peristaltic stimulants, piperidinediones, progestogens, prolactin inhibitors, prostaglandins, protease inhibitors, proton pump inhibitors, psychoneurotopic agents, psychopharmacological drugs, psychotherapeutic agents, pyschotropics, quinazolone derivatives, respiratory agents, respiratory stimulants, rhinitis drugs, sedatives, somnifacients, selective serotonin reuptake inhibitors, sexual hormones, skeletal muscle relaxants, smoking cessation agents, sore throat and mouth treatments, periodontal disease treatments, statins, stomachics, styptic agents, sympatholytics, systemic anti-infective agents, nonsystemic anti-infective agents, terine relaxants, thrombolytic agents, thyroid preparations, antithyroid preparations, thyroid hormones, tranquilizers, tranquilizer antipsychotics, treatments for acute radiation exposure, treatments for attention-deficit hyperactivity disorder, treatments for glaucoma, treatments for gout, treatments for Sjorgren's syndrome, tremor preparations, ulcer treatments, uricosuric agents, urinary tract agents, vaccines, vasoconstrictors, vasodilators, vasopressors, and veterinary drugs. For example, in some embodiments, a pharmaceutical agent included in an oral dispersible film described herein is 2'-deoxycytidine 5'-monophosphate, 2':3'-cyclic monophosphate, 2'-deoxyadenosine 5'5-triphosphate, 2'-deoxyadenosine 5'-monophosphate, 2'-deoxyguanosine 5'-monophosphate, 3',5'-cyclic monophosphate, 5'-monophosphate, 8B/9A-substituted oestra-L 3,5(10)-triene, acetaminophen, acycloguanosine, adenosine 3',5'-cyclic monophosphate, alaproclate, alexidine, alfacalcidol, almotriptan, alprazolam, ambrisentan, ambroxol, ambroxol hydrochloride, amitriptyline hydrochloride, amlodipine, amobarbital, amphotericin B, apomorphine, aprepitant, aripipazole, ascorbic acid, asenapine, aspirin, atenolol, atomoxetine, ATP, avitriptan, azasetron, azathioprine, batanopride, benzalkonium chloride, benzocaine, benzonatate, beta-histine, betamethasone, betaxolol, bis-biguanide, bretazenil, bromazepam, brompheniramine maleate, buprenorphine, buprenorphine hydrochloride, caffeine, caramiphen edisylate, carbemazepime, carbinoxamine maleate, cetirizine, cetirizine hydrochloride, cetyl pyridium chloride, cetylpyridinium chloride, chlophedianol hydrochloride, chlordiazepoxide, chlorhexidine, chlorhexidine digluconate and tetracaine combination, chlorpheniramine, chlorpromazine, cimetidine, ciprofloxacin, citalopram, clebopride, clemastine fumarate, clonazepam, clonixine, clozapine, cobamamide, codeine, cyclobenzaprine, cyclophosphamide, cytidine 5'-monophosphate, dalfampridine, dasatinib, dazopride, D-chlorpheniramine maleate, dapoxetine, dapoxetine and tadalafil, deferiprone, delmopinol, desloratadine, dexchlorpheniramine maleate, dexketoprofen, dextromethorphan, dextromethorphan hydrobromide, diazepam, diclofenac, diclofenac sodium, diclofenac potassium, dicyclomine hydrochloride, diflunisal, dimenhydrinate, diphenhydramine citrate, diphenhydramine hydrochloride, diphenylpyraline hydrochloride, dolasetron, domiphen bromide, domperidone, donepezil hydrochloride, doxylamine succinate, dronabinol, dutasteride, EDTA, eletriptan, enalapril, enzalutamide, enoxacin, erlotinib, estazolam, estradiol, etoricoxib, everolimus, exemestane, ezetimibe, eszopiclone, famotidine, fenoprofen calcium, fentanyl, finasteride, fingolimod, flumazenil, flurazepam, fluorides, fluoxetine, fluvoxamine, frovatriptan, galantamine, glatiramer acetate, growth hormone releasing peptide-2, glimepiride, granisetron, grepafloxacin, guaifenesin, guanosine 2':3'-cyclic monophosphate, guanosine 2'-monophosphate, guanosine 3',5'-cyclic monophosphate, guanosine 3'-monophosphate, guanosine 5'-monophosphate, haloperidol, hexetidine, hydrocodone, hydrocortisone, hydromorphone, ibuprofen, imatinib, imipramine hydrochloride, indomethacin, inosine 5'-monophosphate, iodine, ipecac, isopropyl antipyrine, itasetron, ketoprofen, ketotifen, ketotifen fumarate, lansoprazole, lenalidomide, L-argenin, levobetaxolol hydrochloride, levodopa, levofloxacin, levorphanol, levosulpiride, levothyroxine, linaclotide, lisinopril, liothyronine, L-lysine, lomefloxacin, loperamide, loperamide hydrochloride, loratidine, lorazepam, lormetazepam, L-valine, meclizine, mecobalamin, mefanamic acid, melatonin, melatonin analog, meloxicam, memantine, mequitazine, methadone, methylphenidate, metoclopramide, metophon, metopimazine, montelukast sodium, morphine, morphine sulfate, inosine 5'-monophosphate, nabilone, nalidixic acid, nalorphine, naloxone, naloxone hydrochloride dehydrate, naltrexone, naproxen, naratriptan, neramexane, nicotine, nicotine analog, nicotinic acid, nifedipine, nilvadipine, nimesulide, nisin formulations, nitrazepam, nitroglycerin, N-tetradecyl-4-ethylpyridinium chloride, nystatin, octapinol, octenidine, olanzapine, omeprazole, ondansetron, ondansetron base, orbifloxacin, oseltamivir carboxylate, oxazolam, oxybutinine, oxycodone, oxymorphone, palonosetron, pancopride, paracetamol, paroxetine, pentobarbital, phenols, phenylephrine, phenylpropanolamine, picosulfate sodium, piroxicam, potassium iodide, pramipexole, prednisolone, prelanenant, prochlorperazine, progesterone, progestin, promethazine hydrochloride, pronase, propranolol, propiverine, propoxyphene, pseudoephredrine hydrochloride, pyrilamine maleate, quaternary ammonium salts, romasetron, ranitidine, rasigiline, remacemide, repaglinide, risperidone, rivaroxaban, rivastigmine, rivastigmine tartrate, rizatriptan, roflumilast, ropinirole, rosuvastatin, roxithromycin, salbutamol, salicylanilide, salivary gland hormone, sanguinarine, scopolamine, selegiline, serrapeptase, sertraline, sildenafil, sildenafil citrate, simethicone, sinvastatine, solifenacin, streptodornase, streptokinase, structural homolog of adenosine 5' monophosphate, sulfonamide, sulpiride, sumatriptan, sunitinib, tadalafil, tapentadol, tecfidera, tegafur, teriflunomide, terpin hydrate, tetradecylpyridinium chloride, tetrahydrolipstatin, thalidomide, thiamazole, thiocolchicine derivatives, timidazole, tocopherol nicotinate, tolmetin sodium, topiramate, tramadol hydrochloride, triazolam, triclosan, trihexyphenidyl, trimetazidine, trimethobenzamide, tripelennamine citrate, tripolyphosphate sodium, triprolidine hydrochloride, tropisetron, umatriptan, uridine 5'-monophosphate, valproic acid, vardenafil, vardenafil hydrochloride, vareniclina, vinpocetine, xanthone, xycodone, zatosetron, zinc compounds, zinc histidine, zolmitriptan, or zolpidem. Combinations of pharmaceutical agents (e.g., those described herein) may also be used in a single oral dispersible film preparation.

In certain embodiments, a nutraceutical agent or supplement is included in an oral dispersible film described herein. In certain embodiments, the oral dispersible film can be designed such that a nutraceutical agent or supplement included therein has a local effect. In certain embodiments, the oral dispersible film can be designed such that a nutraceutical agent or supplement included therein is absorbed by the oral mucosa. In certain embodiments, the oral dispersible film can be designed such that a nutraceutical agent or supplement included therein mimics the pharmacokinetics of a traditional dosage form (e.g., an oral dosage form), such as a marketed dosage form, such as a capsule or tablet. Non-limiting examples of nutraceutical agents and supplements that may be included in an oral dispersible film described herein include anesthetics, antibacterials, steroids, anticaries agents, anti-cavity ingredients, anti-gingivitis agents, anti-inflammatory agents, antioxidants, antiperspirants, antiplaque agents, antitussives, cold prevention agents, cold and allergy treatments, cough treatments, dermatological agents, diarrhea treatments, enzymes, erectile dysfunction treatments, female sexual dysfunction treatments, heartburn and dyspepsia agents, hemostatics, herbals, hydration agents, oral hygiene treatments, periodontal actives, periodontal disease drugs, pH control agents, plaque disclosing agents, pre-treatment and treatment for exposure to chemical weapons, provitamins, respiratory disorder treatments, sleep aids, smoking cessation, sore throat agents, stimulants, stomatitis therapies, tartar control agents, vaccines, vitamin derivatives, vitamin extracts, and vitamins. For example, in some embodiments, a nutraceutical agent or supplement included in an oral dispersible film described herein is acerola, electrolytes, aloe, aluminum, amino acids, anise, antibiotics, antimicrobial essential oil, apple extract, arsenic, balsam pear, barium chlorite, benzocaine, beta-carotene, beta-glucans, bicarbonate, bioflavonoids, biotene (glucose oxidase lactose peroxidase and lysozyme), biotin, blueberry, boron, breath freshening agents, bromine, buckwheat, cadmium, calcium, calcium chlorite, calcium peroxide, carbohydrates, carbonate, carvacrol, catechol, cevimeline, chitosan, chlorides, chlorine, chlorine dioxide, choline, chromium, cinnamon, citral, cobalt, coenzyme Q10, copper, DHA, edible organic acid, EPA, erythritol, essential oils, eucalyptol, evening primrose, fluorine, folic acid, garlic, geraniol, germinated unpolished rice, ginkgo leaf, glucose tolerance factor chromium, glutathione, glycerin, grapefruit extracts, green tea, green tea extracts, guava sesame, herb extracts, herbs, hinokitiol, huperzine-A, hydrogen peroxide, hydrogen peroxide adduct of carbodiimide persulfate, hydroperoxide, inositol, iodine, iron, isomaltulose, kava-kava extract (e.g., standardized to 30% kavalactones), lactitol, lactobacillus, lithium, lithium chlorite, magnesium, magnesium chlorite, maltitol powdered hydrogenated glucose syrup, manganese, mannitol, manose, matrimony vine (e.g. lychium Chinese), melatonin, menthol, meswak extract, metal chlorite, methylsalicylate, minerals, molybdenum, molybdenum nickel, momordicae fructus, mugwort, mulberry leaf, niacin (vitamin B3), niacin amide, oils, organic peroxides, PABA, pantethine, pantothenic acid, papain, parched bean flour, peppermint, perborate salt, perboric acid, percarbonate salt, perilla, peroxide generating compounds, peroxyacids, peroxycarbamate, persulfate salt, persulfates, phenol, phosphate ions, phosphorus, pilocarpine, polyalcohol, potassium, potassium chlorite, protein, PVP-hydrogen peroxide complex, pyridoxine (vitamin B6), red ginseng extracts, riboflavin, rose hip, seaweed extracts, selenium, silicon, sodium, sodium chlorite, sorbitol, soybean isoflavone, spearmint, strontium, sugar, superoxide dismutase, sweet tea, tea tree oil, thiamine, thyme oil, thymol, tin, tree and plant components/extracts, turmeric, eucalyptol, vanadium, vanadium glutathionine, vitamin A, vitamin B complex, vitamin B1, vitamin B12, vitamin B2, vitamin B6, vitamin C, vitamin D, vitamin D3, vitamin E, vitamin K, vitamin P, vitamins, wintergreen, or zinc.

Other agents that may be included in oral dispersible films described herein include antidotes, antigens or allergens, recombinant allergens, allergoids, antimicrobial agents, antiperspirants, antiseptics, anti-smoking formula, aromatizing agents, botanicals, breath deodorizing agents, breath freshening agents, breath masking agents, Chinese medicines, comfort agents, conditioning agents, cosmetic agents, deodorant actives, diet formula, dyes, emollients, flavor masking agents, flavors, food products, fragrances, heating agents, humectants, insects, malodor control agents, minerals, moisturizers, mouthwash components, oral band, oral freshness formula, proteins, refreshment agents, saliva stimulating agents, sexual enhancement formula, sugars, veterinary agents, whitening agents, wound-burn protective agents, wound-healing drugs, and homeopathic medicines.

The amount of an agent (e.g. pharmaceutical agent, nutraceutical agent, supplement, or cosmetic agent) or combinations thereof included in a provided oral dispersible film will depend on the indication target population. In some embodiments, a provided oral dispersible film contains an effective amount of an agent. The term "effective amount" as used herein, refers to a sufficient amount of agent to produce a desired outcome. The exact amount required will vary from subject to subject, depending on the species, age, and general condition of the subject, the indication, the particular agent, and the like. In some embodiments, when the agent is a pharmaceutical agent or nutraceutical agent, the oral dispersible film contains a therapeutically effective amount of the agent. The term "therapeutically effective amount" as used herein refers to a sufficient amount of a pharmaceutical or nutraceutical agent to achieve the intended purpose, such as, for example, to cause a reduction of symptoms of a disease.

It will be understood that the total daily usage of film described herein may be decided by an attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001).

In certain embodiments, a provided film may be administered to the oral mucosa or other mucous membranes where they are rapidly disintegrated by saliva and/or other aqueous materials on the mucosal surface. In certain embodiments, upon disintegration, a provided film releases one or more agents (e.g., pharmaceutical agent, nutraceutical agent, supplement, or cosmetic agent) to the mucous membranes. A provided film may be administered in such a manner so as to deliver an effective amount of an agent.

Hydrophilic polymers tend to easily absorb surrounding moisture, leading to a structural modification of the polymer matrices regarding their mechanical and physical properties. The oral dispersible films based on hydrophilic polymers tend to became sticky and less ductile over time. Indeed, it is necessary to strictly control relative humidity during the manufacture of traditional oral dispersible films. In certain embodiments, oral dispersible films provided herein are more hydrophobic in order to decrease sensitivity to humidity.

The relative hydrophobicity/hydrophilicity of a membrane surface is commonly determined by contact angle measurements. This property is characterized by a small liquid droplet resting on a flat horizontal solid/liquid surface. In hydrophilic materials the droplet completely spread out on the solid surface and the contact angle tend to be 0°, since the liquid is strongly attracted to the solid surface. In turn, less hydrophilic materials present higher contact angles closest to 90°. Generally, highly hydrophilic surfaces have contact angles of 0° to 30°, whereas highly hydrophobic surfaces have water contact angles as high as 150° or even nearly 180°. Regarding to these surfaces, the water droplets do not actually wet the surface at any significant extent which would compromise the disintegration of the oral dispersible film. In certain embodiments, a desirable oral dispersible film provided herein relies in a balance between these properties, elevated contact angle and enough wettability for rapid disintegration.

In certain embodiments, an orodispersible film described herein has a rapid disintegration time. In certain embodiments, an orodispersible film described herein has a disintegration time less than or equal to 90 seconds. In certain embodiments, an orodispersible film described herein has a disintegration time less than or equal to 60 seconds. In certain embodiments, an orodispersible film described herein has a disintegration time less than or equal to 45 seconds. In certain embodiments, an orodispersible film described herein has a disintegration time less than or equal to 30 seconds. In certain embodiments, an orodispersible film described herein has a disintegration time less than or equal to 20 seconds. In certain embodiments, an orodispersible film described herein has a disintegration time less than or equal to 15 seconds. In certain embodiments, an oral dispersible film described herein has a disintegration time less than or equal to 10 seconds. In certain embodiments, an oral dispersible film described herein has a disintegration time less than or equal to 8 seconds. In certain embodiments, an orodispersible film described herein has a disintegration time less than or equal to 5 seconds.

In certain embodiments, a provided film has a thickness in the range of about 20 µm to about 1200 µm. In certain embodiments, a provided film has a thickness of about 20 µm, about 50 µm, about 75 µm, about 100 µm, about 125 µm, about 150 µm, about 175 µm, about 200 µm, about 225 µm, about 250 µm, about 300 µm, about 400 µm, about 500 µm, about 600 µm, about 700 µm, about 800 µm, about 900 µm, or about 1000 µm. In any of the foregoing embodiments, the film may be a monolayer.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

An exemplary preparation is described below.

In certain embodiments, a solution is prepared by dissolving a disintegrant and a stabilizer in ultra-purified water or in a mixture of water and ethanol. After complete dissolution a plasticizer is added, and the solution is kept under magnetic stirring at high shear rate, e.g., for at least 1 hour. A film forming polymer solution is added and the high shear rate agitation is maintained, e.g., for 2 hours. The final solution is maintained until complete homogeneity. In certain embodiments, when additives such as colorants, flavors, or sweeteners are included in the formulation, they are added prior to film forming polymer addition. In certain embodiments, the procedure is performed at room temperature.

In certain embodiments, film solutions are cast in release lines (substrate) with a film applicator. To adjust for different heights a vertically adjustable doctor knife may be used and film solutions are cast, e.g., with speeds of 18 mm/s. In certain embodiments, a provided film is cast with a gap of 250-500 µm. In certain embodiments, cast films are dried in an appropriate equipment, e.g., at 40° C., until dryness. The duration of dryness depends on the properties of the formulation and polymer.

Example 1

The disintegrant (NaCMC) and the stabilizer (HPMC or PVA) are dissolved in ultra-purified water or in a mixture of water and ethanol. The solution can be heated for PVA fast dissolution. After their completely dissolution, the plasticizer is added, and the solution is kept under magnetic agitation at high shear rate, for at least 1 hour. Finally, the PVAc dispersion is added and the high shear rate agitation is maintained for more 2 hours. The film solution is cast in release liners (substrate) with a film applicator. To adjust to different heights a vertically adjustable doctor knife is used and the film solutions are cast with a maximum speed of 18 mm/s. The films are cast with a gap of 250-500 µm, but preferentially at 300 µm. The cast films are dried at 40° C. The duration of dryness depends on the properties of each polymer.

TABLE 1

Rapid disintegration films with high contact angle containing PVAc dispersion, a stabilizer (PVA), a disintegrant (NaCMC) and a plasticizer (Triethylcitrate); laboratory preparation.

| | Films | | | |
|---|---|---|---|---|
| | 1 | 2 | 1 | 2 |
| | mixture (g) | | % w/w film | |
| PVAc dispersion (Kollicoat SR 30D) | 2.45 | 3.14 | 43.46% | 55.16% |
| PVA (Mowiol 4-88) | 0.30 | 0.26 | 19.54% | 17.09% |
| Triethylcitrate | 0.26 | 0.15 | 17.43% | 10.68% |
| NaCMC (Blanose) | 0.30 | 0.26 | 20.57% | 17.07% |
| Water | 9.78 | 7.37 | | |
| Young's Modulus (Mpa) | 577.3 | 678.5 | | |
| Elongation (%) | 9.53 | 45.82 | | |
| Tensile strength | 7.04 | 9.80 | | |
| Water content (%) | 6.875 | 5.470 | | |

TABLE 1-continued

Rapid disintegration films with high contact angle containing PVAc dispersion, a stabilizer (PVA), a disintegrant (NaCMC) and a plasticizer (Triethylcitrate); laboratory preparation.

| | Films | | | |
|---|---|---|---|---|
| | 1 | 2 | 1 | 2 |
| | mixture (g) | | % w/w film | |
| Disintegration time (s) | 5 | 7 | | |
| Contact angle (°) | 89.18 | 72.69 | | |

Example 2

The disintegrant (NaCMC) and the stabilizer (HPMC or PVA) are added to 80% of the quantity of the ultra-purified water under stirring. The solution can be heated for PVA fast dissolution. After their completely dissolution and cooling, the additives (citric acid, mannitol, sucralose, mono-ammonium glycyrrhizinate) and the other 20% of the water are added under stirring for at least 1 hour or until complete dissolution. The PVAc dispersion is added at higher shear rate and maintained for at least 2 hours. The film solution is cast with a film applicator preferentially at 300 μm. The cast films are dried at 40° C. The duration of dryness depends on the properties of each polymer.

TABLE 2a

Rapid disintegration oral films with high contact angle containing a mixture of the main film-forming components, flavors, sweeteners, colorants, other additives; laboratory preparation (amounts given in grams).

| | Films | | | | | | | |
|---|---|---|---|---|---|---|---|---|
| | 3 | 4 | 5 | 6 | 7 | 8 | 9 | 10 |
| | mixture (g) | | | | | | | |
| PVAc dispersion (Kollicoat SR 30D) | 2.98 | 3.27 | 2.52 | 3.33 | 3.32 | 2.38 | 2.51 | 2.74 |
| PVA (Mowiol 4-88) | 0.26 | 0.11 | 0.23 | 0.23 | 0.11 | 0.29 | 0.32 | 0.31 |
| Triethylcitrate | 0.11 | 0.16 | | 0.15 | 0.02 | | | |
| PEG 6000 | | | | | | 0.24 | 0.21 | 0.15 |
| NaCMC (Blanose) | 0.27 | 0.22 | 0.23 | 0.10 | 0.22 | 0.31 | 0.31 | 0.30 |
| Citric acid | 0.09 | | 0.14 | 0.08 | | 0.02 | 0.02 | 0.03 |
| Mannitol | | 0.08 | 0.15 | | 0.08 | | | |
| Mono-ammonium glycyrrhizinate | | 0.01 | 0.07 | | | | | |
| Sucralose | | | 0.06 | | 0.06 | | | |
| Maltodextrins | | 0.05 | | 0.05 | 0.05 | | | |
| Strawberry flavor | | | | | 0.08 | | | |
| Red iron oxide | | 0.01 | 0.01 | | | | | |
| Water | 4.29 | 1.26 | 4.84 | 0.81 | 1.91 | 2.03 | 2.66 | 2.12 |
| Young's Modulus (Mpa) | 457.4 | 330.2 | 585.9 | 292.4 | 901.4 | 1176.0 | 1042.0 | 1023.0 |
| Elongation (%) | 25.68 | 38.65 | 1.115 | 81.94 | 6.795 | 0.8533 | 0.73 | 0.65 |
| Tensile strength | 10.07 | 2.44 | 9.44 | 3.54 | 23.39 | 13.02 | 8.293 | 8.085 |
| Water content (%) | 4.66 | 3.73 | 5.445 | 3.095 | 4.255 | 6.310 | 4.655 | 4.715 |
| Disintegration time (s) | 13.50 | 17.06 | 28.50 | 17.30 | 46.22 | 16.00 | 10.50 | 11.00 |
| Contact angle (°) | 58.8 | 64.2 | 79.8 | 57.5 | 74.4 | 53.5 | 73.8 | 73.6 |

TABLE 2b

Rapid disintegration oral films with high contact angle containing a mixture of the main film-forming components, flavors, sweeteners, colorants, other additives; laboratory preparation (amounts given in % w/w).

| | Films | | | | | | | |
|---|---|---|---|---|---|---|---|---|
| | 3 | 4 | 5 | 6 | 7 | 8 | 9 | 10 |
| | % w/w film | | | | | | | |
| PVAc dispersion (Kollicoat SR 30D) | 52.8% | 58.9% | 43.2% | 59.9% | 59.9% | 43.1% | 44.3% | 48.1% |
| PVA (Mowiol 4-88) | 16.8% | 7.0% | 14.6% | 15.2% | 7.2% | 19.5% | 20.9% | 20.4% |
| Triethylcitrate | 6.9% | 10.6% | | 10.0% | 1.3% | | | |
| PEG 6000 | | | | | | 15.8% | 13.8% | 9.8% |
| NaCMC (Blanose) | 17.4% | 14.5% | 14.5% | 6.9% | 14.5% | 20.5% | 20.0% | 19.7% |

TABLE 2b-continued

Rapid disintegration oral films with high contact angle containing a mixture of the main film-forming components, flavors, sweeteners, colorants, other additives; laboratory preparation (amounts given in % w/w).

| | Films | | | | | | | |
|---|---|---|---|---|---|---|---|---|
| | 3 | 4 | 5 | 6 | 7 | 8 | 9 | 10 |
| | | | | % w/w film | | | | |
| Citric acid | 6.0% | | 9.1% | 5.0% | | 1.2% | 1.0% | 2.0% |
| Mannitol | | 5.0% | 9.5% | | 5.1% | | | |
| Mono-ammonium glycyrrhizinate | | 0.5% | 4.7% | | | | | |
| Sucralose | | | 3.9% | | 4.0% | | | |
| Maltodextrins | | 3.0% | | 3.0% | 3.0% | | | |
| Strawberry flavor | | | | | 5.0% | | | |
| Red iron oxide | | 0.4% | 0.5% | | | | | |

Example 3

The disintegrant (NaCMC) and the stabilizer (HPMC or PVA) are dissolved in ultra-purified water or in a mixture of water and ethanol. The solution can be heated for PVA fast dissolution. After their completely dissolution, the plasticizer is added, and the solution is kept under magnetic agitation at high shear rate, for at least 1 hour. The Shellac aqueous solution is added and the high shear rate agitation is maintained for more 2 hours. The film solution is cast in release liners (substrate) with a film applicator preferentially at 300 μm. The cast films are dried at 40° C. until dryness. The duration of dryness depends on the properties of each polymer.

TABLE 3

Rapid disintegration films with high contact angle containing Shellac aqueous solution, a stabilizer (HPMC), a disintegrant (NaCMC) and a plasticizer (PEG 6000, PEG 1000, or 1,2-propanediol); laboratory preparation.

| | Films | | | | | | | |
|---|---|---|---|---|---|---|---|---|
| | 11 | 12 | 13 | 14 | 11 | 12 | 13 | 14 |
| | mixture (g) | | | | % w/w film | | | |
| Shellac (Aquagold) | 3.15 | 3.58 | 3.57 | 3.79 | 51.4% | 57.4% | 57.9% | 59.8% |
| HPMC E5 | 0.30 | 0.26 | 0.30 | 0.30 | 19.6% | 17.0% | 19.7% | 18.9% |
| 1,2-propanediol PEG 6000 | 0.17 | 0.24 | 0.02 | | 11.4% | 15.5% | 1.1% | |
| PEG 1000 | | | | 0.01 | | | | 0.8% |
| NaCMC (Blanose) | 0.27 | 0.16 | 0.33 | 0.32 | 17.6% | 10.1% | 21.2% | 20.5% |
| Water | 3.01 | 1.99 | 7.69 | 7.62 | | | | |
| Young's Modulus (Mpa) | 306.46 | 106.75 | 997.1 | 773.7 | | | | |
| Elongation (%) | 1.01 | 2.69 | 0.475 | 0.48 | | | | |
| Tensile strength | 4.31 | 4.00 | 5.39 | 3.81 | | | | |
| Water content (%) | 5.15 | 4.69 | 4.64 | 5.26 | | | | |
| Disintegration time (s) | 4.0 | 18.0 | 7.0 | 6.5 | | | | |

Example 4

The disintegrant (NaCMC) and the stabilizer (PVA) are dissolved in ultra-purified water or in a mixture of water and ethanol. The solution can be heated for PVA fast dissolution. After their completely dissolution, the plasticizer is added, and the solution is kept under magnetic agitation at high shear rate, for at least 1 hour. Finally, the Methacrylate copolymer dispersion is added and the high shear rate agitation is maintained for more 2 hours. The film solution is cast in release liners (substrate) with a film applicator. To adjust to different heights a vertically adjustable doctor knife is used and the film solutions are cast with speeds of 18 mm/s. The films are cast with a gap of 250-500 μm, but preferentially at 400 μm. The cast films are dried at 40° C. The duration of dryness depends on the properties of each polymer.

TABLE 4

Rapid disintegration films with high contact angle containing Methacrylate copolymer, a stabilizer (PVA), a disintegrant (NaCMC) and a plasticizer (Glycerol); laboratory preparation.

|  | Films | | | | | |
|---|---|---|---|---|---|---|
|  | 15 | 16 | 17 | 18 | 19 | 20 |
|  | mixture (g) | | | | | |
| Eudragit RL 30D | 2.760 | 2.510 | 2.490 | 3.030 | 2.748 | 2.420 |
| Glycerol | 0.150 | 0.300 | 0.220 | 0.160 | 0.155 | 0.140 |
| Blanose | 0.147 | 0.098 | 0.151 | 0.301 | 0.298 | 0.261 |
| Mowiol 4-88 | 0.300 | 0.307 | 0.302 | 0.149 | 0.228 | 0.199 |
| Citric acid |  |  |  |  |  | 0.030 |
| Lemon flavor |  |  |  |  |  | 0.077 |
| Sucralose |  |  |  |  |  | 0.057 |
| NHDC |  |  |  |  |  | 0.015 |
| Yellow Iron Oxide |  |  |  |  |  | 0.001 |
| Titanium dioxide |  |  |  |  |  | 0.001 |
| Water | 2.593 | 2.055 | 2.647 | 6.150 | 6.341 | 5.236 |
| Young's Modulus (Mpa) | 450.70 | 161.20 | 219.50 | 488.20 | 596.01 |  |
| Elongation (%) | 11.67 | 6.98 | 7.49 | 4.03 | 5.62 |  |
| Tensile Strength (Mpa) | 2.99 | 31.58 | 7.25 | 0.63 | 17.18 |  |
| Water Content (%) | 5.98 | 5.95 | 5.29 | 6.45 | 7.75 |  |
| Disintegration time (s) | 19.00 | 19.00 | 44.50 | 33.00 | 27 | 57 |
| Contact Angle (°) | 61.12 | 61.24 | 63.54 | 69.61 |  |  |
|  | % w/w film | | | | | |
| Eudragit RL 30D | 58.1% | 51.6% | 52.6% | 59.8% | 54.71% | 48.16% |
| Glycerol | 10.5% | 20.6% | 15.5% | 10.5% | 10.31% | 9.31% |
| Blanose | 10.3% | 6.7% | 10.6% | 19.8% | 19.80% | 17.34% |
| Mowiol 4-88 | 21.0% | 21.1% | 21.3% | 9.8% | 15.17% | 13.18% |
| Citric acid |  |  |  |  |  | 1.99% |
| Lemon flavor |  |  |  |  |  | 5.10% |
| Sucralose |  |  |  |  |  | 3.79% |
| NHDC |  |  |  |  |  | 1.00% |
| Yellow Iron Oxide |  |  |  |  |  | 0.06% |
| Titanium dioxide |  |  |  |  |  | 0.06% |

Example 5

The disintegrant (NaCMC) and the stabilizer (PVA) are added to 80% of the quantity of the ultra-purified water under stirring. The solution can be heated for PVA fast dissolution. After their completely dissolution and cooling the additives (mannitol, sucralose, flavor, NHDC, citric acid, citrate tri-sodium), the drug substance and the other 20% of the water are added under stirring for at least 1 hour or until complete dissolution. The PVAc dispersion is added at higher shear rate and maintained for at least 2 hours. The film solution is cast with a film applicator, The cast films are dried at 40° C. The duration of dryness depends on the properties of each polymer.

TABLE 5

Rapid disintegration films containing drug substances; laboratory preparation.

| | Films | | | | | |
|---|---|---|---|---|---|---|
| | 21 | 22 | 23 | 24 | 25 | 26 |
| | mixture (g) | | | | | |
| Kollicoat SR 30D | 2.96 | 3.22 | 2.86 | 2.86 | 2.22 | 1.95 |
| Mowiol 4-88 | 0.20 | 0.23 | 0.23 | 0.23 | 0.18 | 0.16 |
| Blanose | 0.20 | 0.21 | 0.15 | 0.23 | 0.17 | 0.15 |
| Triethylcitrate | 0.09 | 0.07 | 0.05 | 0.07 | 0.06 | 0.06 |
| Citric acid | 0.07 | 0.08 | 0.08 | 0.07 | 0.03 | 0.03 |
| Mannitol | 0.10 | 0.05 | 0.08 | 0.07 | 0.05 | 0.04 |
| Citrate tri-sodium | | | | | 0.03 | 0.02 |
| Lemon flavor | | | | | 0.04 | 0.03 |
| Sucralose | | | | | 0.04 | 0.03 |
| NHDC | | | | | 0.01 | 0.01 |
| Pramipexole | 0.05 | 0.02 | 0.17 | 0.08 | 0.30 | 0.45 |
| Water | 9.22 | 3.71 | 3.86 | 4.28 | 3.54 | 3.23 |
| Young's Modulus (Mpa) | 89.42 | 211.4 | 89.98 | 67.41 | 27.32 | 99.95 |
| Elongation (%) | 42.61 | 34.83 | 41.89 | 26.19 | 65.12 | 19.89 |
| Tensile Strength (Mpa) | 10.05 | 10.81 | 8.425 | 7.330 | 2.09 | 1.46 |
| Water Content (%) | 4.745 | 4.035 | 5.000 | 5.430 | 6.98 | 7.56 |
| Disintegration time (s) | 12.50 | 15.00 | 12.50 | 8 | 18.50 | 17.5 |
| | % w/w film | | | | | |
| Kollicoat SR 30D | 53.1% | 57.4% | 51.1% | 51.4% | 40.0% | 34.9% |
| Mowiol 4-88 | 13.1% | 14.9% | 14.9% | 15.0% | 12.0% | 10.4% |
| Blanose | 13.5% | 14.1% | 10.0% | 15.1% | 11.3% | 9.9% |
| Triethylcitrate | 6.3% | 4.5% | 3.0% | 4.4% | 4.0% | 3.8% |
| Citric acid | 4.5% | 5.0% | 5.0% | 4.5% | 2.2% | 1.9% |
| Mannitol | 6.5% | 3.0% | 5.0% | 4.5% | 3.2% | 2.8% |
| Citrate tri-sodium | | | | | 1.8% | 1.6% |
| Lemon flavor | | | | | 2.4% | 2.1% |
| Sucralose | | | | | 2.4% | 2.1% |
| NHDC | | | | | 0.7% | 0.6% |
| Pramipexole | 3.1% | 1.0% | 11.0% | 5.0% | 20.0% | 29.9% |

Example 6

The disintegrant (NaCMC) and the stabilizer (PVA) are added to 80% of the quantity of the ultra-purified water under stirring. The solution can be heated for PVA fast dissolution. After their completely dissolution and cooling the additives (sucralose, flavor, NHDC, citric acid, citrate tri-sodium), the drug substance and the other 20% of the water are added under stirring for at least 1 hour or until complete dissolution. The Methacrylate copolymer dispersion is added at higher shear rate and maintained for at least 2 hours. The film solution is cast with a film applicator. The cast films are dried at 40° C. The duration of dryness depends on the properties of each polymer.

TABLE 6

Orodispersable films with Methacrylate copolymer containing drug substances; laboratory preparation.

| | Films | | | | | | | |
|---|---|---|---|---|---|---|---|---|
| | 27 | 28 | 29 | 30 | 27 | 28 | 29 | 30 |
| | | mixture (g) | | | | % w/w film | | |
| Eudragit RL 30D | 2.734 | 2.720 | 2.679 | 1.923 | 54.40% | 54.12% | 53.62% | 38.62% |
| Glycerol | 0.160 | 0.159 | 0.151 | 0.107 | 10.60% | 10.55% | 10.04% | 7.14% |
| Blanose | 0.295 | 0.293 | 0.290 | 0.208 | 19.57% | 19.44% | 19.34% | 13.89% |
| Mowiol 4-88 | 0.225 | 0.225 | 0.217 | 0.155 | 14.93% | 14.91% | 14.49% | 10.33% |
| Pramipexole | 0.008 | 0.015 | 0.038 | 0.450 | 0.51% | 0.99% | 2.51% | 30.02% |
| Water | 5.800 | 5.793 | 5.730 | 4.716 | | | | |
| Young's Modulus (Mpa) | 395.22 | 577.62 | 457.63 | 110.85 | | | | |
| Elongation (%) | 5.62 | 7.73 | 4.1 | 21.80 | | | | |
| Tensile Strength (Mpa) | 11.39 | 16.85 | 13.3 | 7.11 | | | | |
| Water Content (%) | 6.46 | 6.88 | 6.5 | 7.82 | | | | |
| Disintegration time (s) | 25 | 45.5 | 38.6 | 75.5 | | | | |

TABLE 7

Orodispersable films with Methacrylate copolymer containing drug substances and additives; laboratory preparation.

| | Films | | | | | | | |
|---|---|---|---|---|---|---|---|---|
| | 31 | 32 | 33 | 34 | 31 | 32 | 33 | 34 |
| | | mixture (g) | | | | % w/w film | | |
| Eudragit RL 30D | 1.710 | 1.460 | 1.230 | 0.970 | 33.70% | 29.11% | 24.36% | 19.35% |
| Glycerol | 0.098 | 0.081 | 0.074 | 0.054 | 6.42% | 5.41% | 4.88% | 3.61% |
| Blanose | 0.188 | 0.157 | 0.131 | 0.105 | 12.38% | 10.47% | 8.65% | 6.95% |
| Mowiol 4-88 | 0.143 | 0.118 | 0.097 | 0.082 | 9.39% | 7.87% | 6.43% | 5.48% |
| Citric acid | 0.021 | 0.018 | 0.016 | 0.013 | 1.40% | 1.20% | 1.02% | 0.84% |
| Lemon flavour | 0.055 | 0.046 | 0.039 | 0.031 | 3.64% | 3.08% | 2.54% | 2.04% |
| Sucralose | 0.041 | 0.034 | 0.029 | 0.023 | 2.71% | 2.29% | 1.89% | 1.52% |
| NHDC | 0.011 | 0.009 | 0.008 | 0.006 | 0.71% | 0.60% | 0.50% | 0.40% |
| Yellow Iron Oxide | 0.001 | 0.001 | 0.000 | 0.000 | 0.05% | 0.04% | 0.03% | 0.03% |
| Titanium dioxide | 0.001 | 0.001 | 0.000 | 0.000 | 0.05% | 0.04% | 0.03% | 0.03% |
| Pramipexole | 0.450 | 0.600 | 0.752 | 0.899 | 29.56% | 39.89% | 49.66% | 59.76% |
| Water | 4.610 | 4.189 | 3.805 | 3.604 | | | | |
| Disintegration time (s) | 80.5 | 57.7 | 60.5 | 28.5 | | | | |

Example 7

Example 7 describes exemplary formulations.

Formulation A

| Category | | Component | % by weight | Exemplary range |
|---|---|---|---|---|
| Film forming polymer | present | Polyvinyl acetate (PVAc) dispersion | 30-95% | 30-60% |
| Stabilizer | present | Polyvinyl alcohol (PVA) or Hydroxypropylmethyl cellulose (HPMC) | 1-21% | 5-17.5% |
| Disintegrant | present | Carboxymethylcellulose sodium | 1-22% | 6-22% |

| Category | | Component | % by weight | Exemplary range |
|---|---|---|---|---|
| Plasticizer | optional § | Triethylcitrate (or other citrate derivative) or glycerol or propylene glycol or polyethylene glycol | 0-30% | 0-17% |
| Sweetener | optional § | Sucralose or acesulfame K or mannitol | 0-10% | 0-10% |
| | optional § | Monoammonium glycyrrhizinate or neohesperidin dihydrochalcone (NHDC) | 0-5% | 0-5% |
| Colorant | optional ¥ | ... | 0-1% | 0-1% |
| Flavor | optional ¥ | ... | 0-10% | 0-5% |
| Saliva stimulant | optional ¥ | ... | 0-10% | 0-7% |
| Taste-masking | optional ¥ | ... | 0-60% | 0-10% |
| Buffer system | optional ¥ | ... | 0-15% | 0-10% |
| Drug substance | optional ¥ | ... | 0.001-60% | 0-60% |

§ A wide range of components can be selected as described herein; only exemplary ones are listed.
¥ A wide range of components can be selected as described herein.

Formulation A1

| | |
|---|---|
| PVAc dispersion | 50% |
| NaCMC | 15% |
| PVA 4-88 | 15% |
| Triethylcitrate | 5% |
| Citric acid | 7% |
| NHDC | 1% |
| Sucralose | 1% |
| Flavor | 5% |
| Colorant | 1% |

Formulation B

| Category | | Component | % by weight | Exemplary range |
|---|---|---|---|---|
| Film forming polymer | present | Shellac | 30-95% | 50-60% |
| Stabilizer | present | Polyvinyl alcohol (PVA) or Hydroxypropylmethyl cellulose (HPMC) | 1-21% | 5-17.5% |
| Disintegrant | present | Carboxymethylcellulose sodium | 1-22% | 10-22% |
| Plasticizer | optional § | Triethylcitrate (or other citrate derivative) or glycerol or propylene glycol or polyethylene glycol | 0-30% | 0-15.5% |
| Sweetener | optional § | Sucralose or acesulfame K or mannitol | 0-10% | 0% |
| | optional § | Monoammonium glycyrrhizinate or neohesperidin dihydrochalcone (NHDC) | 0-5% | 0% |
| Colorant | optional ¥ | ... | 0-1% | 0% |
| Flavor | optional ¥ | ... | 0-10% | 0% |
| Saliva stimulant | optional ¥ | ... | 0-10% | 0% |
| Taste-masking | optional ¥ | ... | 0-60% | 0% |
| Buffer system | optional ¥ | ... | 0-15% | 0% |
| Drug substance | optional ¥ | ... | 0.001-60% | 0% |

§ A wide range of components can be selected as described herein; only exemplary ones are listed.
¥ A wide range of components can be selected as described herein.

Formulation B1

| | |
|---|---|
| Shellac | 53% |
| NaCMC | 17.5% |
| HPMC | 20% |
| Propylene glycol | 9.5% |
| NHDC | 0% |
| Sucralose | 0% |
| Flavor | 0% |
| Colorant | 0% |

Formulation C

| Category | | Component | % by weight | Exemplary range |
|---|---|---|---|---|
| Film forming polymer | present | Methacrylate copolymer dispersion | 19-95% | 19-60% |
| Stabilizer | present | Polyvinyl alcohol (PVA) or hydroxypropylmethyl cellulose (HPMC) | 1-21% | 5-17.5% |
| Disintegrant | present | Carboxymethylcellulose sodium | 1-22% | 6-20% |
| Plasticizer | optional § | Triethylcitrate (or other citrate derivative) or glycerol or propylene glycol or polyethylene glycol | 0-30% | 3-21% |
| Sweetener | optional § | Sucralose or acesulfame K or mannitol | 0-10% | 0-4% |
| | optional § | Monoammonium glycyrrhizinate or neohesperidin dihydrochalcone (NHDC) | 0-5% | 0-1% |
| Colorant | optional ¥ | ... | 0-1% | 0-0.12% |
| Flavor | optional ¥ | ... | 0-10% | 0-5% |
| Saliva stimulant | optional ¥ | ... | 0-10% | 0-2% |
| Taste-masking | optional ¥ | ... | 0-60% | 0% |
| Buffer system | optional ¥ | ... | 0-15% | 0-2% |
| Drug substance | optional ¥ | ... | 0.001-60% | 0-60% |

§ A wide range of components can be selected as described herein; only exemplary ones are listed.
¥ A wide range of components can be selected as described herein.

Formulation C1

| | |
|---|---|
| Methacrylate copolymer dispersion | 57.5% |
| NaCMC | 9.9% |
| PVA 4-88 | 18.5% |
| Glycerol | 14% |
| NHDC | 0% |
| Sucralose | 0% |
| Flavor | 0% |

We claim:

1. An orodispersible film comprising (i) a film forming polymer, wherein the film forming polymer is polyvinyl acetate, wherein the concentration of the polyvinyl acetate in the orodispersible film is between 30% and 95% by weight; (ii) a disintegrant; and (iii) polyvinyl alcohol (PVA) or hydroxypropylmethyl cellulose (HPMC).

2. The orodispersible film of claim 1, wherein the disintegrant is (i) a cellulose derivative, (ii) a cellulose ether, (iii) carboxymethylcellulose or a salt thereof, or (iv) sodium carboxymethylcellulose.

3. The orodispersible film of claim 1 further comprising one or more dispersants.

4. The orodispersible film of claim 3, wherein the one or more dispersants comprise one or more of (i) sodium lauryl sulfate, (ii) povidone, (iii) macrogol cetostearyl ether, and (iv) sorbic acid and sodium hydroxide.

5. The orodispersible film of any one of claims 1 and 3 further comprising a plasticizer.

6. The orodispersible film of claim 5, wherein the plasticizer is (i) a citrate derivative, (ii) triethylcitrate, (iii) glycerol, (iv) polyethylene glycol, or (v) propylene glycol.

7. The orodispersible film of claim 1, wherein the concentration of at least one of the polyvinyl alcohol or hydroxypropylmethyl cellulose in the orodispersible film is between 5% and 17.5% by weight.

8. The orodispersible film of claim 1 further comprising one or more of (i) one or more sweeteners, (ii) one or more colorants, (iii) one or more flavoring agents, and (iv) one or more saliva stimulants.

9. The orodispersible film of claim 1, wherein:
the concentration of the polyvinyl alcohol or hydroxypropylmethyl cellulose, in the orodispersible film, is between 1% and 21% by weight; and
the disintegrant is sodium carboxymethylcellulose, wherein the concentration of the sodium carboxymethylcellulose in the orodispersible film is between 1% and 22%; by weight
wherein the total percentage by weight of all the components of the orodispersible film does not exceed 100%.

10. The orodispersible film of claim 9, wherein the concentration of the polyvinyl acetate in the orodispersible film is between 30% and 60% by weight.

11. The orodispersible film of claim 10, wherein the concentration of the polyvinyl alcohol or hydroxypropylmethyl cellulose, in the orodispersible film, is between 5% and 17.5% by weight.

12. The orodispersible film of claim 11 further comprising a plasticizer.

13. The orodispersible film of claim 1 further comprising an active agent that is a pharmaceutical agent, a nutraceutical agent, a supplement, or a cosmetic agent.

14. A method of delivering an orodispersible film of claim 1 comprising placing the orodispersible film into the oral cavity for a sufficient period of time to disintegrate.

15. The orodispersible film of claim 1, wherein the disintegration time of the orodispersible film upon contacting oral mucosa is less than or equal to 90 seconds.

16. The orodispersible film of claim 1, wherein the disintegration time of the orodispersible film upon contacting oral mucosa is less than or equal to 45 seconds.

17. The orodispersible film of claim 1, wherein the concentration of the polyvinyl acetate in the orodispersible film is between 30% and 60% by weight.

18. The orodispersible film of claim 1, wherein the concentration of the disintegrant in the orodispersible film is between 1% and 22% by weight.

19. The orodispersible film of claim 1, wherein the concentration of the disintegrant in the orodispersible film is between 5% and 17.5% by weight.

20. The orodispersible film of claim 1, wherein the concentration of at least one of the polyvinyl alcohol or hydroxypropylmethylcellulose in the orodispersible film is between 1% and 21% by weight.

21. The orodispersible film of claim 1, wherein the concentration of at least one of the polyvinyl alcohol or hydroxypropylmethylcellulose in the orodispersible film is between 5% and 17.5% by weight.

22. The orodispersible film of claim 3, wherein the concentration of the one or more dispersants in the orodispersible film is between 0.001% and 10% by weight.

23. The orodispersible film of claim 5, wherein the concentration of the plasticizer in the orodispersible film is between 1% and 20% by weight.

24. The orodispersible film of claim 1, wherein the polyvinyl alcohol or hydroxypropylmethylcellulose is polyvinyl alcohol.

25. The orodispersible film of claim 1, wherein the polyvinyl alcohol or hydroxypropylmethylcellulose is hydroxypropylmethylcellulose.

26. The orodispersible film of claim 1, wherein the ratio of: (1) the concentration of polyvinyl acetate in the orodispersible film to (2) the concentration of the polyvinyl alcohol or hydroxypropylmethyl cellulose, in the orodispersible film, is between 20:1 and 1:2, by weight.

27. The orodispersible film of claim 9 further comprising an active agent that is a pharmaceutical agent, a nutraceutical agent, a supplement, or a cosmetic agent.

* * * * *